United States Patent
Komaki et al.

[11] Patent Number: 5,932,555
[45] Date of Patent: Aug. 3, 1999

[54] TERPENOID COMPOUND 0406TP-1

[75] Inventors: Hisayuki Komaki, Chiba-ken; Akira Nemoto, Ibaraki-ken; Yasushi Tanaka, Chiba-ken; Yuzuru Mikami, Chiba-ken; Katsukiyo Yazawa, Chiba-ken; Jun'ichi Kobayashi, Sapporo, all of Japan

[73] Assignee: Higeta Shoyu Co., Ltd., Tokyo, Japan

[21] Appl. No.: 09/010,589

[22] Filed: Jan. 22, 1998

[30] Foreign Application Priority Data

Jan. 23, 1997 [JP] Japan ................................ 9-023109
Sep. 10, 1997 [JP] Japan ................................ 9-261106

[51] Int. Cl.$^6$ .......................... C12P 19/35; A61K 31/71; C07M 15/00
[52] U.S. Cl. ........................ 514/25; 435/74; 435/78; 514/53; 536/4.1; 536/17.9; 536/18.1
[58] Field of Search ................... 536/4.1, 18.1, 536/17.9; 435/74, 78; 514/25, 53

[56] References Cited

FOREIGN PATENT DOCUMENTS 0 808 843  11/1997  European Pat. Off. .

OTHER PUBLICATIONS

Kino, Toru et al., "FK–506, a novel immunosuppressant isolated from a streptomyces.", The Journal of Antibiotics, vol. XL, No. 9, pp. 1249–1255 (1987).

Borel, J.F. et al., "Biological effects of cyclosporin A: a new antilymphocytic agent.", Agents and Action, vol. 6, No. 4, pp. 468–475 (1976).

Mikami, Yuzuru et al., "Susceptibility patterns of pathogenic nocardia to some selected antimicrobial agents and their usefulness in the identification work in a clinical laboratory.", JFCC, vol. 5, pp. 89–95 (1989).

Hatanaka, Hiroshi et al., "FR–900520 and FR–900523, novel immunosuppressants isolated from a streptomyces.", The Journal of Antibiotics, vol. XLI, No. 11, pp. 1592–1601 (1988).

Fujita, Tetsuro et al., "Fungal metabolites. Part 11. A potent immunosuppressive activity found in *Isaria sinclairii* metabolite.", The Journal of Antibiotics, vol. 47, No. 2, pp. 208–215 (1994).

*Primary Examiner*—Elli Peselev
*Attorney, Agent, or Firm*—Browdy and Neimark

[57] ABSTRACT

The present invention relates to compound 0406TP-1 represented by the general formula (I):

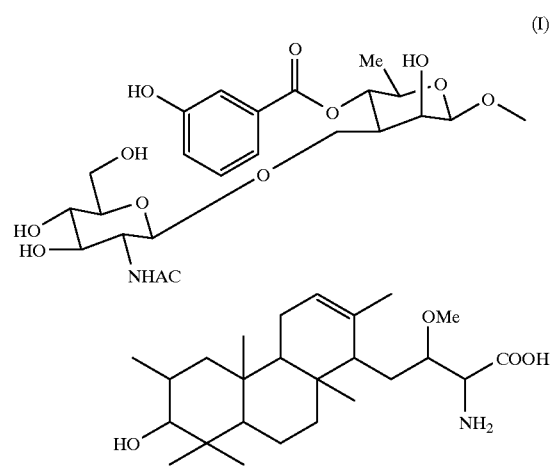

wherein Ac represents an acetyl group and Me represents a methyl group, or a pharmaceutically acceptable salt thereof, having excellent antitumor activity and immunosuppressive activity.

5 Claims, No Drawings

TERPENOID COMPOUND 0406TP-1

DETAILED DESCRIPTION OF THE INVENTION

1. Technical Field to Which the Invention Belongs

The present invention relates to novel compound 0406TP-1 and a process for producing the same, as well as uses thereof. Novel compound 0406TP-1 is an unknown terpenoid compound isolated and purified from a culture of microorganisms, particularly actinomycetes, and has an excellent physiological activity, particularly an excellent antitumor activity and immunosuppressive activity.

Accordingly, the novel terpenoid compound of the present invention can be utilized effectively as a therapeutic agent and/or preventive agent against cancer as an antitumor agent. Further, the novel terpenoid compound of the present invention can be utilized effectively as an immunosuppressive agent, for example for inhibition of rejection in transplantation of organs and skin, and as a therapeutic agent and/or preventive agent for autoimmune diseases.

2. Prior Art

A large number of novel compounds have been discovered as antitumor agents, and novel compounds have also been synthesized and some of them are practically used.

Certainly several types of excellent antitumor agents have been known among conventionally known antitumor agents, but there are desire for further development of not only effect but also safety and productivity.

Recently, immunosuppressive agents are used against a group of morbid states called allergic diseases, collagen disease, autoimmune diseases or connective tissue diseases, and their effects draw much attention. Similarly, they are also applied to rejection in transplantation of organs such as liver, heart, kidney etc. and their importance is increasing from year to year.

As a substance developed as a chemical with high specificity and selectivity toward a certain type of immune cells in this field, cyclosporin A (A. Rciegger et al., Agents and Actions, vol. 6, pp. 468–475 (1976)) has been developed, and it has been revealed that cyclosporin A inhibits production of interleukin 2 (IL-2) from helper T cells, but does not inhibit production of IL-2 from suppressor T cells, and as a result, prevents rejection of the transplant. At present, this compound achieves significant effects in transplantation of organs such as kidney, bone marrow etc. and is clinically used.

However, it has been noted that this chemical suffers from problems such as causing side effects depending on case, including acute poisoning of kidney, light degree of neural lesion, thickening of gum etc.

Further, macrolide antibiotic tacrorims (FK506) found in 1984 (T. Kino et al., J. Antibiot., vol. 40, pp. 1249–1255 (1987)) has achieved preferable results as an immunosuppressive agent. However, it has problems with tacrorims productivity etc., such as low productivity and simultaneous production of a trace amount of tacrorims-related substances to place a possible limit to developments in the future, while there are obstacles to the pancreas and kidney, and the site of its action is similar to that of cyclosporin A, so there has been strong demand for development of a novel substance of higher safety having a different site of action.

PROBLEM TO BE SOLVED BY THE INVENTION

The present invention was made to respond to such demand in this field and as a result of their extensive screening in line with technical development of antitumor agents and immunosuppressive agents, it was found that a novel compound not known up to now has antitumor activity and immunosuppressive activity, leading to completion of the present invention. The present invention was made for the purpose of providing a novel compound having superior antitumor activity and a novel compound having superior immunosuppressive activity to conventional known substances.

MEANS TO SOLVE THE PROBLEM

For the purpose of obtaining a novel substance having antitumor activity and a novel substance having immunosuppressive activity, the present inventors conducted screening of a wide variety of natural substances, particularly metabolites from microorganisms, and as a result of screening for substances having more effective antitumor activity and immunosuppressive activity, they found that *Nocardia brasiliensis* IFM 0406 (FERM BP-5498) produces a substance having both antitumor activity and immunosuppressive activity in the culture. They confirmed this substance to be a novel substance not known up to now by further examining its physicochemical properties in detail and revealing its chemical structure. This substance was a novel compound of terpenoid represented by the general formula (I) as described in claim 1. The present inventors named this compound 0406TP-1.

That is, the present invention relates to novel compound 0406TP-1 represented by the general formula (I):

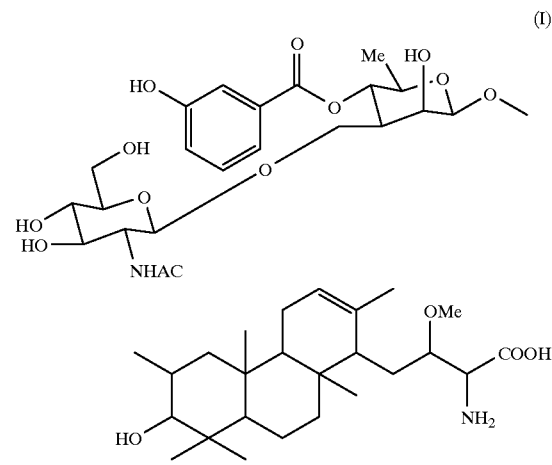

wherein Ac represents an acetyl group and Me represents a methyl group, as well as pharmaceutically acceptable salts thereof.

The present invention further relates to a novel antitumor agent and immunosuppressive agent comprising novel terpenoid compound 0406TP-1 or a pharmaceutically acceptable salt thereof. Hereinafter, the present invention is described in detail.

EMBODIMENTS FOR CARRYING OUT THE INVENTION

The physicochemical properties of compound 0406TP-1 of the present invention are shown in Table 1 below. Table 1. Physicochemical properties of compound 0406TP-1
(1) Color and state of the substance: white powder
(2) Specific rotation: $[\alpha]^{30}_D$: +15.0° (c=0.50, $CH_3OH$)
(3) Infrared absorption spectrum Its significant signals are as follows:

FT-IR (KBr) $\nu_{max}$: 3432, 2934, 1676, 1454, 1378, 1291, 1203, 1075, 893, 839, 801, 755, 722, 570 cm$^{-1}$ (4) Ultraviolet absorption spectrum Its significant signals are as follows:

$\lambda_{max}$ (in CH$_3$OH): 212 ($\epsilon$15000), 239 ($\epsilon$5200), 300 ($\epsilon$1900) nm (5) Molecular formula and FAB-MS Molecular formula: $C_{45}H_{68}N_2O_{16}$ HR-FAB-MS (positive, glycerol matrix) m/z:

Found: 893.4646 (M+H)$^+$

Calculated: 893.4647

(6) $^1$H nuclear magnetic resonance spectrum

Its significant signals are as shown in Tables 2 and 3.

(7) $^{13}$C nuclear magnetic resonance spectrum

Its significant signals are as shown in Tables 2 and 3.

(8) Solubility: Soluble in water, methanol and ethanol. Insoluble in ethyl acetate, acetone chloroform and ether.

Significant signals among $^1$H NMR and $^{13}$C NMR spectra of the compound are shown in Tables 2 and 3.

TABLE 2

$^1$H and $^{13}$C NMR data of Compound 0406TP-1 (CD$_3$OD) (1) (a: δ [in ppm])

| position | $^1$H$^a$ | J (Hz) | $^{13}$C$^a$ | |
|---|---|---|---|---|
| 1(a) | 1.49 m | | 44.53 | t |
| (b) | 1.82 m | | | |
| 2 | 3.73 t | 9.0 | 80.31 | d |
| 3 | 3.06 d | 9.7 | 83.83 | d |
| 4 | | | 41.70 | s |
| 5 | 1.69 m | | 19.22 | t |
| 6(a) | 1.69 m | | 46.75 | t |
| (b) | 1.78 m | | | |
| 7 | 1.41 m | | 31.78 | t |
| 8 | | | 39.05 | s |
| 9 | 1.32 m | | 47.87 | d |
| 10 | | | 38.09 | s |
| 11 | 1.93 brs | | 27.57 | t |
| 12 | 5.39 brs | | 124.08 | d |
| 13 | | | 139.04 | s |
| 14 | 1.61 m | | 52.81 | d |
| 15(a) | 1.41 m | | 32.46 | t |
| (b) | 1.49 m | | | |
| 16 | 3.81 dd | 11.4, 3.3 | 81.07 | d |
| OMe | 3.53 s | | 58.90 | q |
| 17 | 4.46 d | 3.5 | 55.36 | d |
| 18 | | | 170.62 | s |
| 19 | 0.97 s | | 17.82 | q |
| 20 | 1.04 s | | 29.74 | q |
| 21 | 1.14 s | | 29.42 | q |
| 22 | 1.09 s | | 23.06 | q |

TABLE 3

$^1$H and $^{13}$C NMR data of Compound 0406TP-1 (CD$_3$OD) (2) (a: δ [in ppm])

| position | $^1$H | J (Hz) | $^{13}$C | |
|---|---|---|---|---|
| 23 | 1.69 s | | 23.13 | q |
| 1' | 5.06 d | 1.1 | 103.62 | d |
| 2' | 4.46 dd | 3.1, 1.1 | 72.60 | d |
| 3' | 4.12 dd | 9.8, 3.1 | 80.35 | d |
| 4' | 5.31 t | 9.8 | 74.64 | d |
| 5' | 4.05 dq | 9.8, 6.2 | 68.58 | d |
| 6' | 1.16 d | 6.2 | 18.30 | q |
| 7' | | | 167.50 | s |
| 8' | | | 132.96 | s |
| 9' | 7.51 t | 1.4 | 117.94 | d |
| 10' | | | 159.50 | s |

TABLE 3-continued $^1$H and $^{13}$C NMR data of Compound 0406TP-1 (CD$_3$OD) (2) (a: δ [in ppm])

| position | $^1$H | J (Hz) | $^{13}$C | |
|---|---|---|---|---|
| 11' | 7.10 dd | 7.6, 1.4 | 122.04 | d |
| 12' | 7.38 t | 7.6 | 131.38 | d |
| 13' | 7.59 dd | 7.6, 1.4 | 122.50 | d |
| 1" | 4.58 d | 8.5 | 104.54 | d |
| 2" | 3.58 dd | 10.0, 8.5 | 58.02 | d |
| NHAc | 1.54 s | | 23.42 | q |
| | | | 174.55 | s |
| 3" | 3.41 dd | 10.1, 8.1 | 75.80 | d |
| 4" | 3.35 m | | 72.33 | d |
| 5" | 3.33 m | | 78.30 | d |
| 6"(a) | 3.73 d | 11.6 | 63.07 | t |
| (b) | 3.93 dd | 11.6, 1.6 | | |

Compound 0406TP-1 of the present invention is produced by e.g. *Nocardia brasiliensis* IFM 0406 (FERM BP-5498).

The microbiological characteristics of *Nocardia brasiliensis* IFM 0406 are that morphologically, it has branched long hyphae and aerial hyphae as observed in one kind of actinomycetes when cultured in an oatmeal agar medium (ISP No. 3). By extending the culture time, a few of bacilliform spores and fragmentation of aerial hyphae and vegetative hyphae were observed. Since the fragmentation of vegetative hypha was observed, it was estimated morphologically to belong to the genus Nocardia.

The cultural characteristics of *Nocardia brasiliensis* IFM 0406 in various media are shown in Table 4 below. The physiological characteristics are shown in Table 5.

TABLE 4

Cultural characteristics of *Nocardia brasiliensis* IFM 0406

| Medium | Characteristics |
|---|---|
| ISP-2 (yeast extract-malt extract agar) | vigorous growth, wrinkles on the surface, pale ocher |
| ISP-3 (oatmeal agar) | moderate growth, smooth surface, white yellow vigorous white aerial hyphae |
| ISP-4 (inorganic salts-starch agar) | No or little growth |
| ISP-5 (glycerol-asparagine agar) | moderate growth, smooth surface, gray trace aerial hyphae |
| ISP-6 (peptone-yeast extract-iron agar) | vigorous growth, wrinkles on the surface, pale brown |
| BHI (brain heart infusion agar) | vigorous growth, wrinkles on the surface, pale ocher |
| SDA (Sabouraud's dextrose agar) | vigorous growth, wrinkles on the surface, pale yellow trace aerial hyphae |

TABLE 5

Physiological characteristics of *Nocardia brasiliensis* IFM 0406

Decomposition

| | |
|---|---|
| adenine | negative |
| casein | positive |
| hypoxanthine | positive |
| tyrosine | positive |
| xanthine | negative |

TABLE 5-continued

Physiological characteristics of *Nocardia brasiliensis* IFM 0406

Production of acid from sugar

| | |
|---|---|
| galactose | positive |
| glucose | positive |
| inositol | positive |
| rhamnose | negative |
| maltose | negative |
| adonitol | negative |
| arabinose | negative |
| erythritol | negative |
| mannose | negative |
| sorbitol | negative |
| Utilization of citric acid | negative |

Susceptibility to antibiotics

| | |
|---|---|
| imipenem | negative |
| tobramycin | positive |
| 5-FU | negative |
| β-lactamase production | positive |
| Growth limit temperature | no growth at 45° C. |

The present strain was cultured in a medium (brain heart infusion containing 2% glucose) with shaking at 250 rpm at 30° C. for 72 hours, and the cells grown in the medium were harvested by centrifugation (3000 rpm×10 minutes) and washed twice with distilled water. Further, the cells were washed with ethanol and then dried under vacuum to give the dry cells. The amino acid composition, sugar composition and lipid composition of the cell wall of this dried cells were examined on the basis of Bergey's Manual of Determinative Bacteriology, 9th ed., Williams, Baltimore, 1993. Meso-diaminopimelic acid was detected by the amino acid analysis, and arabinose and galactose were detected by the sugar analysis. The presence of mycolic acid was confirmed from the result of the lipid analysis, and its type was Nocardia type. Isoprenoid quinone i.e. a bacterial lipid component was confirmed to contain MK-8 (H4) cycle as a major component and MK-8 (H4), MK-8 (H) and MK-9 (H2) as trace components. The present strain was identified as *Nocardia brasiliensis*, further from its ability to assimilate, casein, hypoxanthine and tyrosine and from its production pattern of acid from sugar and its susceptibility pattern to antibacterial agents as shown in Table 5 (Mikami & Yazawa, Susceptibility pattern of pathogenic Nocardia to some selected antimicrobial agents and their usefulness in the identification work in a clinical laboratory: Bull. JFCC "Bulltein of the Japan Federation for Culture Collections", 5:89–95, 1989).

The result of examination of the G+C content and DNA homology as shown in Table 6 also supported that the present microorganism is *Nocardia brasiliensis*.

TABLE 6

G + C content and DNA homology of *Nocardia brasiliensis* IFM 0406

| | G + C Content (mol %) | DNA homology (%) | | |
|---|---|---|---|---|
| | | *Nocardia brasiliensis* IFM 0236T | *Nocardia transvalensis* IFM 0333T | *Nocardia bransiliensis* IFM 0406 |
| N. brasiliensis IFM 0236T | 68.1 | 100 | NT | 100 |
| N. transvalensis IFM 0333T | 69.0 | NT | 100 | 25 |
| N. brasiliensis IFM 0406 | 68.0 | 94 | 8 | 100 |

The present strain is thus classified into *Nocardia brasiliensis*, and it was an outstanding characteristic of the present strain to produce compound 0406TP-1. *Nocardia brasiliensis* IFM 0406 was deposited under FERM BP-5498 on Apr. 3, 1996 under the Budapest Treaty with the National Institute of Bioscience and Human-Technology, Agency of Industrial Science and Technology, Japan.

It has been confirmed that compound 0406TP-1 of the present invention is produced not only by *Nocardia brasiliensis* IFM 0406 (FERM BP-5498) but also by other strains belonging to the genus Nocardia, and production of compound 0406TP-1 in the present invention encompasses use of a wide variety of all mutants capable of producing compound 0406TP-1, including artificial mutants obtainable from these microorganisms by subjecting them to mutation treatment using e.g. X-ray irradiation, γ-ray irradiation, nitrogen mustard, N-methyl-N'-nitro-N-nitrosoguanidine, 2-aminopurine, ethylmethane sulfonate etc. as well as spontaneous mutants.

The novel compound 0406TP-1 of the present invention represented by the general formula (1) can be produced not only by chemical synthesis methods but also by microorganisms as described above.

In the latter case, the novel compound 0406TP-1 of the present invention represented by the general formula (1) can be produced by a microorganism producing said compound and belonging to the genus Nocardia, such as *Nocardia brasiliensis* IFM 0406, in a medium containing a carbon source and nitrogen source capable of being assimilated by the microorganism, preferably under aerobic submerged culture conditions (e.g. shake culture, aeration agitation culture etc.).

The carbon source used is preferably glucose, glycerol, sucrose, starch, dextrin and other carbohydrates.

The nitrogen source used is preferably oatmeal, yeast extract, beef extract, tuna meat extract, peptone, gluten meal, cottonseed powder, soybean meal, corn steep liquor, dried yeast, wheat germ, peanut powder, chicken bone meat meal etc., and further inorganic and organic nitrogen-containing compounds such as ammonium salts (e.g. ammonium nitrate, ammonium sulfate, ammonium phosphate etc.), urea, amino acids etc. can also be used advantageously.

It is of advantage to use these carbon and nitrogen sources in combination, where these are not necessarily pure for use. This is because some impure sources contain growth factors and trace elements so their use is desired.

If necessary, inorganic salts such as sodium carbonate, potassium carbonate, sodium phosphate, potassium phosphate, sodium chloride, potassium chloride, sodium iodide, potassium iodide, magnesium salts, capper salts, cobalt salts etc. can be added to the medium.

If necessary, particularly where the medium will foam, an antifoaming agent such as fluid paraffin, animal oil, vegetable oil, mineral oil, silicon etc. can be added.

For large-scale industrial production of the object substance, culture under aeration with agitation in a manner similar to the case of other fermentation products is preferable. In the case of small-scale production, shake culture in a flask is preferable.

If culture is conducted in a large tank, it is preferable to inoculate the producing microorganism into a relatively small amount of medium and then transfer the culture to a large production tank where it is cultured for production, thus preventing the growth of the microorganism from being delayed in the step of producing compound 0406TP-1.

In this case, the compositions of the pre-culture and production media may be the same or may, if necessary, be different.

Culture is carried out preferably under aeration and agitation by known methods using e.g. propellers and other apparatuses, rotation or shake in a fermenter, pump treatment, air blowing etc. Air for aeration is preferably sterilized.

Although the culture temperature may be altered suitably within the range in which 0406TP-1-producing microorganisms produce said compound, they are cultured usually at 10 to 40° C., preferably 25 to 35° C.

Although the period of culture varies depending on culture conditions and culture volume, the period is usually about 1 day to 1 week.

After fermentation is finished, the desired compound 0406TP-1 is recovered from the culture. That is, the cells are subjected directly to extraction with water or an organic solvent, or are first disrupted mechanically or by known means such as ultrasonication and then subjected to extraction with water and/or an organic solvent, followed by recovery and purification according to conventional methods. In the case of culture broth, direct extraction with solvent may be conducted, or the culture broth may be separated by filtration or centrifugation, concentrated under reduced pressure and lyophilized, and after pH adjustment is conducted, the sample is applied and adsorbed onto carriers such as anion or cation exchange resin, activated charcoal, powder cellulose, silica gel, alumina, adsorption resin etc., followed by elution of compound 0406TP-1 from the carriers.

As the recovery and purification methods, conventional methods for recovery of antibiotics are suitably used, including solvent extraction with water, an organic solvent, or a mixed solvent thereof; chromatography; recrystalization from a single solvent or a mixed solvent; and a combination thereof.

The recovery and purification of compound 0406TP-1 is carried out suitably adopting the known methods described above, for example as follows:

First, the culture is centrifuged or filtrated with an MF membrane to remove the cells and adsorbed onto hydrophobic adsorption resin, and the adsorption fraction is eluted with methanol, and this eluted fraction is concentrated under reduced pressure, further adsorbed onto DEAE chromatograph, and eluted with Tris-HCl buffer. The eluate is concentrated under reduced pressure and further subjected to chromatography again, thus raising the degree of purity, followed by lyophilization if necessary.

In the case of administering compound 0406TP-1 of the present invention as a pharmaceutical preparation, the compound of the present invention is administered as such, or as a pharmaceutical composition containing it at e.g. 0.1 to 99.5%, preferably 0.5 to 90% in a pharmaceutically acceptable non-toxic and inert carrier.

As the carriers, use is made of at least one of solid, semi-solid, or liquid diluent, filler, and other aid for formulation. The pharmaceutical composition is administered preferably in a dosage unit form. The pharmaceutical composition of the present invention can be administered through oral administration, intra-tissue administration, topical administration (transdermal administration etc.), or through the rectum. As a matter of course, the composition should be administered in a preparation form suitable for these administration methods.

The dosage thereof as an antitumor agent or immunosuppressive agent is regulated preferably depending on conditions such as the age, body weight etc. of the patient, administration route, and the type, severeness etc. of the disease. If administered in a large amount, it is administered desirably in portions at intervals per day. Administration is carried out generally at a dosage of about 10 to 2000 mg/day.

Oral administration can be carried out using a solid or liquid dosage unit, for example in the form of powder, powder mixture, tablet, sugar-coated agent, capsule, drops, sublingual tablet etc.

The powder is produced by dividing the active substance into fineness of suitable size. The powder mixture is produced by dividing the active substance into fineness of suitable size and then mixing it with similarly divided pharmaceutical carrier such as edible hydrocarbon such as starch, mannitol etc. Flavoring, preservative, dispersing agent, coloring agent, perfume etc. may also be mixed as necessary.

The capsule is produced by charging capsule outer cover such as gelatin capsule with powder, powder mixture or granules. The present compound in the form of e.g. powder may be filled into such outer cover after it was mixed with lubricant or fluidity agent, such as colloidal silica, talc, magnesium stearate, calcium stearate and solid polyethylene glycol. Addition of disintegrating agent and solubilization agent such as carboxymethylcellulose, calcium carbonate and sodium carbonate can improve the efficacy of the pharmaceutical preparation when taken in the form of capsule. In addition, the finely divided powder of the present compound may be formed into soft capsule by suspending and dispersing it in vegetable oil, polyethylene glycol, glycerin, a surfactant and covering the mixture with a gelatin sheet to produce a soft capsule.

The tablet is produced by preparing a powder mixture, granulating or slagging it and then adding a disintegrating agent or lubricant to it followed by tabletting.

The powder mixture is produced by mixing the suitably powdered materials with the above diluent or base, and if necessary, binder (e.g. sodium carboxymethylcellulose, alginate, gelatin, polyvinyl pyrrolidone, polyvinyl alcohol etc.), dissolution-delaying agent (e.g. paraffin etc.), re-absorber (e.g. quaternary salts) and/or absorption agent (e.g. bentonite, kaolin, dicalcium phosphate) may be used in combination. The powder mixture can be formed into granules by first moistening it with a binder such as syrup, starch paste, gum arabic, cellulose solution or polymer solution and then enforceably passing it through a screen. Instead of granulating it in this manner, the powder may be formed into granules in an alternative manner by introducing it into a tabletting machine and disrupting the resulting slag in an incomplete form into granules.

The granules produced in this manner can be prevented from adhering to one another by adding stearic acid, stearate, talc, mineral oil etc. as lubricant. The mixture thus lubricated is then tabletted. Also, the chemical may be tabletted directly after combined with fluid inert carrier, without forming it into granules or slag as described above. Use may be made of transparent or semi-transparent protective coating made of shellac sealed coating, coating of sugar or polymeric material, and polished coating made of wax.

Other oral administration forms, such as solution, syrup, elixir etc. can also be formed in a dosage unit form so as to contain a predetermined amount. The syrup is produced by dissolving the compound in an aqueous perfuming solution, and the elixir is formulated by suspending the compound in non-toxic alcoholic carrier. A dissolving agent, an emulsifying agent (e.g. ethoxylated isostearyl alcohols, polyoxyethylene sorbitol esters), preservative, a flavor-imparting agent (e.g. peppermint oil, saccharine) and others may also be added as necessary.

If necessary, the dosage unit formulation for oral administration may be formed into microcapsule. This formulation may be coated or filled in polymer, wax etc. to extend its acting period or achieve sustained release.

Parenteral administration can be effected using a liquid dosage unit form for intradermal, intramuscular or intravenous injections, for example in the form of solution or suspension. These are produced by suspending or dissolving a predetermined amount of the compound in non-toxic liquid carrier e.g. aqueous or oily medium suitable to the object of injection and then sterilizing the resulting suspension or solution. Alternatively, a predetermined amount of the compound is placed in a vial and then the vial and its content may be sterilized and sealed. To dissolve or mix it just before administration, preliminary vial or carrier may be prepared along with the powdered or lyophilized active ingredient. A non-toxic salt or salt solution may be added to render the injection isotonic. Further, stabilizer, preservative, emulsifying agent etc. may be used in combination.

Administration into the rectum can be effected using suppository in which the compound is mixed with a solid having a low melting point, such as polyethylene glycol, cacao lipid, higher esters (e.g. myristyl palmitinate) and a mixture thereof.

The efficacy of the novel compound 0406TP-1 of the present invention as a pharmaceutical preparation can be confirmed in various tests.

Antitumor activity can be confirmed by a method of measuring in vitro cytotoxity for cultured tumor cell lines or a method of measuring the degree of survival of mice into which tumor cells have been transplanted.

Immunosuppressive activity can be confirmed by a method of measuring the activity of inhibiting blastgenesis in mouse allogenic mixed lymphocyte reaction (MLR) or by measuring inhibitory effect on induction of cytotoxic T cells due to allogenic cell immunity in vivo in mice.

The safety of compound 0406TP-1 can be confirmed in an acute toxicity test on mice or in a toxicity test by repeated administration.

Hereinafter, the present invention is described in more detail with reference to the Examples, which however not are intended to limit the present invention.

EXAMPLE 1

Production by Fermentation, and Recovery and Purification (1) Production by fermentation Nocardia brasiliensis IFM 0406 (FERM BP-5498) was inoculated into 10 ml basal medium consisting of 2% glycerol, 1% polypeptone (Nippon Seiyaku K.K.) and 0.5% tuna meat extract, pH 7.0 in a 50-ml Erlenmeyer flask and cultured at 30° C. for 72 hours with shaking. The thus-obtained seed culture was inoculated at 1% v/v into 1.5 L of the same medium in a 5-L Erlenmeyer flask and pre-cultured in the same manner as above. The thus-obtained preculture was further inoculated into a 200-L tank fermenter containing 150 L of the same medium and cultured at an aeration rate of 1 vvm at an agitation rate of 200 rpm at 30° C. for 90 hours.

(2) Recovery and purification

The resulting culture, 150 L, was filtered through a filter cloth to remove the cells, and further subjected to microorganism removal by passing it through a microfiltration membrane of 0.45 μm in pore size (Pelicon cassette system, made by Millipore). This filtrate fraction was adsorbed onto Diaion HP20 column (Mitsubishi Chemical Corporation) of 15×100 cm, then sufficiently washed with 50% methanol to remove impurities, and eluted with 20 L of 100% methanol. This eluate fraction was concentrated in an evaporator and lyophilized.

A part of this lyophilized product, 0.5 g, was dissolved in 50 ml of 20 mM Tris-HCl buffer, pH 8.0 and adsorbed onto a DEAE TOYOPEARL 650 M column (2.5×10 cm) and eluted with 500 ml of the same buffer. Detection of compound 0406TP-1 in the eluted fractions was conducted on the basis of data in which the HPLC pattern of each fraction was compared with immunosuppressive activity by mouse allogenic mixed lymphocyte reaction (MLR), thereby eluted fractions containing the compound being collected. Alternatively, eluted fractions containing the compound were collected on the basis of data in which the HPLC pattern of each fraction was compared with the cytotoxicity on cultured tumor cell line P388 and its adriamycin-resistant strain (P388/ADR).

100 ml of the active fraction was collected, adjusted to pH 4.0 with 2 N hydrochloric acid, adsorbed onto a CM TOYOPEARL 650 M column (2.5×10 cm), and eluted with 500 ml of 20 mM acetate buffer, pH 4.0. 100 ml fraction containing compound 0406TP-1 was collected, concentrated into 2 ml in an evaporator, and adsorbed onto CAPCELL-PACK $C_{18}$ SG120 (Shiseido Co., Ltd.) 3×25 cm. Gradient elution (30 ml/min., 60 min.) of from 18% to 50% acetonitrile was carried out using acetonitrile containing 0.15% TFA (trifluoroacetic acid). 20 ml, per fraction, was analyzed by HPLC, and fractions (100 ml in total) containing compound 0406TP-1 were collected, concentrated and dried in vacuo to give 3.6 mg powder.

EXAMPLE 2

Antitumor Activity (1) Cytotoxicity test on cultured tumor cell lines

Cultured tumor cell lines P388 and P388/ADR were suspended in RPMI1640 medium containing 10% heat inactivated fetal calf serum (FCS) and 20 μM 2-mercaptoethanol whereby a cell suspension (5×10⁴ cells/ml) was prepared.

A sample examined was dissolved in methanol, then diluted with RPMI 1640 medium and subjected to serial 2-fold dilution starting at the concentration of 0.1 mg/ml. 180 μl of the cell suspension and 20 μl of the sample solution were added into a 96-well micro-titer plate and incubated at 37° C. in wet 5% $CO_2$ gas/95% air. 72 hours thereafter, cell growth was measured by a calorimetric assay method using 3-(4,5-dimethyl-2-thiazolyl)-2,5-diphenyl-2H-tetrazolium bromide (MTT) as follows: 20 μl of 2 mg/ml MTT solution was added to each well and the cells were incubated for 4 hours at 37° C. Thereafter, 50 μl of 50% dimethylformamide solution containing 20% sodium dodecyl sulfate was added to each well and allowed to stand, so that the formed violet formazan crystal was dissolved, and its absorbance at 570 nm was measured in a microplate absorbance photometer (Immunoreader) and used as an indicator of the growth. The result was expressed in terms of the concentration of a sample at which growth was inhibited by 50% ($IC_{50}$), which was determined from the relationship between sample concentrations and degrees of inhibition calculated using the following equation (1):

Degree of inhibition=[1−(absorbance in presence of sample)/(absorbance in absence of sample)]×100  (1)

The results are shown in Table 7. Compound 0406TP-1 has strong cytotoxicity (antitumor activity) on cultured tumor cells and also has strong inhibition on growth of even antitumor resistant cells (adriamycin-resistant cells), and it was thus confirmed that this compound is effective as an antitumor agent.

TABLE 7

Inhibition of compound 0406TP-1 on growth of tumor cells

| Cell lines | $IC_{50}$ (μg/ml) 0406TP-1 | Adriamycin |
|---|---|---|
| P388 | 0.65 | 0.027 |
| adriamycin-resistant P388 | 0.22 | 0.53 |

(2) In vivo antitumor activity in mice

To examine the in vivo antitumor activity of 0406TP-1, an antitumor test on mice with P388 and P388/ADR transplanted in them was carried out.

Compound 0406TP-1, and Adriacin (generic name, adriamycin, Kyowa Hakko Kogyo Co., Ltd.) as the comparative control, were dissolved in distilled water for injection at 1 mg/ml, 0.5 mg/ml and 0.1 mg/ml respectively and used as test solutions. $2\times10^5$ cells of P388 or P388/ADR were inoculated intraperitoneally into each of $CDF_1$ mice (male, each weighing 20 g, 10 animals/group), and from the next day, the test solution was administered at 10, 5, and 1 mg/kg body weight/day respectively by intraperitoneal injection of 200 μl sample at each concentration once a day for 10 successive days. The numbers with time of mice which survived after administration was counted and the average survival days and T/C (survival days of treated mice/survival days of control mice) were calculated. The average body weights after 10 days were also measured. The results are shown in Table 8.

TABLE 8

Mouse in vivo antitumor test

| transplanted cell line | administered substance | dosage (mg/kg body weight/ day × 10 days) | average survival days | T/C (g) | average body weight after 10 days (%) |
|---|---|---|---|---|---|
| P388 | control | — | 10.4 | 100 | 24.8 |
| P388 | 0406TP-1 | 1 | 12.7 | 123 | 25.9 |
| P388 | 0406TP-1 | 5 | 12.7 | 123 | 26.3 |
| P388 | 0406TP-1 | 10 | 13.2 | 128 | 27.3 |
| P388 | adriamycin | 1 | 12.4 | 120 | 23.2 |
| P388 | adriamycin | 5 | 8.4 | 81 | 15.5 |
| P388 | adriamycin | 10 | 7.8 | 76 | — |
| P388/ADR | control | — | 11.1 | 100 | 26.8 |
| P388/ADR | 0406TP-1 | 1 | 14.4 | 130 | 26.2 |
| P388/ADR | 0406TP-1 | 5 | 14.8 | 133 | 27.3 |
| P388/ADR | 0406TP-1 | 10 | 18.3 | 165 | 26.4 |
| P388/ADR | adriamycin | 1 | 10.7 | 96 | 23.5 |
| P388/ADR | adriamycin | 5 | 7.0 | 63 | — |
| P388/ADR | adriamycin | 10 | 7.5 | 68 | — |

Adriamycin did not show therapeutic effect at a dosage of more than 5 mg/kg body weight/day, due to its toxicity. In the P388-translanted mice, the group given adriamycin (1 mg/kg body weight/day) and the group given 0406TP-1 showed the same degree of therapeutic effect (improvement in survival rate). On the other hand, in the P388/ADR-translanted mice, adriamycin did not show therapeutic effect because of the resistance of the transplanted tumor cells to adriamycin, whereas the group given 0406TP-1 indicated significant therapeutic effect. From these results, it was suggested that 0406TP-1 shows antitumor activity in vivo.

EXAMPLE 3

Immunosuppressive Activity (1) Mouse allogenic mixed lymphocyte reaction [MLR]

A sample was prepared by dissolving the purified 0406TP-1 obtained in Example 1 at a concentration of 1 mg/ml in distilled water and then diluted serially with RPMI 1640.

The mouse allogenic mixed lymphocyte reaction for assay was carried out according to the method of Hatanaka et al. (Hatanaka et al., J. Antibiotics, 41, 1592–1601 (1988)). That is, spleen cells from C57BL/6 mouse ($H-2^b$) as responder cells were mixed with spleen cells from BALB/C mouse ($H-2^d$) treated with mitomycin C as stimulator cells, and then cultured.

Preparation of the responder cells was carried out in the following manner:

The spleen was removed from a 5- to 6-week-old C57BL/6 mouse, then homogenized in 20 ml ice-cold RPMI 1640 medium supplemented with 10% heat inactivated fetal calf serum (FCS), and filtered through a gauze to give a single cell suspension. The cells were recovered by centrifugation, suspended in 4 ml PRMI 1640 medium, followed by adding 6 ml solution (pH 7.2) containing 0.15 M ammonium chloride, 1 mM sodium hydrogen carbonate and 0.1 mM tetrasodium ethylenediaminetetraacetate, and the mixture was incubated at 0° C. for 1 minute to remove the contaminating erythrocytes. After RPMI 1640 medium was added, the cells were centrifuged, washed 3 times with 20 ml of the same medium by centrifugation, and suspended at $5.6\times10^6$ cells/ml in RPMI 1640 medium containing 50 μM 2-mercaptoethanol and 10% FCS to give a responder cell suspension.

For preparation of the stimulator cells, the spleen was removed from a 5- to 6-week-old BALB/C mouse, and 25 μg/ml mitomycin C was added to a spleen cell suspension prepared in the same manner as above, and the cells were incubated at 37° C. for 30 minutes. After 20 ml of PRMI 1640 medium was added, the cells were centrifuged, washed 3 times with the same buffer (20 ml) by centrifugation, and then suspended at $5.6\times10^6$ cells/ml in RPMI 1640 medium containing 50 μM 2-mercaptoethanol and 10% FCS to give a stimulator cell suspension.

90 μl of the responder cell suspension, 90 μl of the stimulator cell suspension and 20 μl of sample were added to a 96-well microplate and incubated at 37° C. in wet 5% $CO_2$/95% air for 96 hours. The blastgenesis of lymphocytes was examined by measuring incorporation of [$^3$H]-thymidine. After 96 hours of incubation, 20 μl of RPMI 1640 medium containing 25 μCi/ml [$^3$H]-thymidine was added to each well and pulse-labeled at 0.5 μCi/well. Further, it was incubated for 4 hours, and the culture was collected on a glass fiber filter in a multiple cell harvester machine. The radioactivity of a filter disk corresponding to each well was determined using liquid scintillation counter (beta-counter). The average of the radioactivity (count per minute: cpm) determined in duplicate for 1 minute per well was calculated, and the result, that is, the degree of inhibition of the incorporation of [$^3$H]-thymidine (blastgenesis), was shown in terms of $IC_{50}$ in Table 9. As the comparative control, the result of cyclosporin A is shown.

TABLE 9

Effect of immunosuppressive agent on MLR

| Substance | $IC_{50}$ (μg/ml) |
|---|---|
| 0406TP-1 | 0.11 |
| cyclosporin A | 0.37 |

(2) Mouse cytotoxic T cell induction test

As the in vivo indicator of immunosuppressive activity, the inhibitory effect of 0406TP-1, and a commercial immunosuppressive agent i.e. cyclosporin A as the comparative control, on induction of cytotoxic T cells by allogenic immunization in mice was examined. The test was carried out according to the method of Fujita et al. (Fujita et al., J. Antibiotics, 47, 208–215 (1994)). A 8-week-old, female C57BL/6 mouse (H-$2^b$) was immunized intraperitoneally with 0.2 ml of cultured cell line P815 suspension ($5\times10^7$ cells/ml PBS) derived from DBA/2 (H-$2^d$), and 0.2 to 0.3 ml of 0.1 mg/ml sample was administered intraperitoneally at a dosage of 1 mg/kg body weight/day for 5 days including the day of immunization.

The spleen was removed from the mouse on Day 9 after immunization, then homogenized in 20 ml RPMI 1640 medium supplemented with 10% FCS and filtered through a gauze. After recovery by centrifugation, the cells were suspended in 4 ml RPMI 1640 medium, followed by adding 6 ml solution (pH 7.2) containing 0.15 M ammonium chloride, 1 mM sodium hydrogen carbonate and 0.1 mM tetrasodium ethylenediaminetetraacetate, and the sample was incubated at 0° C. for 1 minute to remove contaminating erythrocytes. After addition of 20 ml RPMI 1640 medium, the cells were centrifuged and further washed 3 times with the same buffer by centrifugation, and suspended in RPMI 1640 medium supplemented with 10% FCS to form a single cell suspension which was then used as effector cells. As the target cells, P815 was incubated at 37° C. for 3 hours in Dulbecco's Minimum Essential Medium (D-MEM) containing 0.1 μCI $Na_2^{51}CRO_4$ so that $^{51}Cr$ was incorporated into the cells, which were then washed 3 times with 20 ml D-MEM by centrifugation, followed by being suspended at $2\times10^5$ cells/ml in RPMI 1640 medium supplemented with 10% FCS. To measure cytotoxic T cell activity, 100 μl of the effector cell suspension and 100 μl of the target cell suspension were put to each well on a 96-well round-bottomed microplate and incubated at 37° C. for 4 hours, and the cells were centrifuged and the amount of $^{51}Cr$ released into the supernatant was measured and the cytotoxic T cell activity was calculated using the following equation 2:

$$\text{Cytotoxic T cell activity} = A/B \times 100 \quad (2)$$

A: (radioactivity of effector cells+target cells)− (radioactivity of only target cells)

B: (radioactivity of target cells treated with 0.1 N HCl)− (radioactivity of only target cells)

The cytotoxic T cell activity was expressed in terms of lytic unit (LU). One LU is defined as the number of effector cells required for 20% lysis of $2\times10^4$ target cells, and the result is shown in LU per spleen.

Similarly, the mouse was immunized and then administered 0.2 to 0.3 ml of 1 mg/ml of the sample (i.e. at a dosage of 10 mg/kg body weight/day) by intraperitoneal administration for 5 days and the cytotoxic activity was determined. The results are shown in Table 10.

TABLE 10

In vivo cytotoxic T cell induction test on mice

| Substance | Dosage (mg/kg body weight/ day × 5 days) | Cytotoxic T cell activity | |
|---|---|---|---|
| | | LU/spleen | inhibition (%) |
| control | — | 400 | 0 |
| 0406TP-1 | 1.0 | 350 | 12 |
| cyclosporin A | 1.0 | 399 | 0 |
| control | — | 461 | 0 |
| 0406TP-1 | 10 | 285 | 38 |
| cyclosporin A | 10 | 355 | 23 |

Compound 0406TP-1 was shown to inhibit induction of cytotoxic T cells in spleen cells in an allogenic-immunized mouse by intraperitoneal administration. This indicates that the rejection occurring in transplanting organs etc. can be inhibited (immuno-suppressived).

EXAMPLE 4

Toxicity Test (1) Acute toxicity test

Compound 0406TP-1 was dissolved at 10 mg/ml in 5% aqueous glucose solution and used as test solution. Compound 0406TP-1 was administered at a dosage of 100 mg/kg body weight by injecting 200 μl of the test solution intravenously into each of five ICR mice (SPF, male, each weight: 20 g). During observation of survival of the animals with time for one month after administration, they all survived. Therefore, $LD_{50}$ value by single administration of 0406TP-1 intravenously was calculated to be >100 mg/kg body weight. From this result, the low toxicity and safety of this compound were suggested.

(2) Repeated administration toxicity test

Compound 0406TP-1 was dissolved at 1 mg/ml, 0.5 mg/ml, and 0.1 mg/ml in distilled water for injection and used as test solutions. As the comparative control, test solutions of adriamycin were prepared in the same manner. Each test solution was administered into $CDF_1$ mice (male, each weight: 21 to 22 g, 10 animals/group) at 10, 5, and 1 mg/kg body weight/day by intraperitoneal injection of 210 to 220 μl (total for 10 days) of the solution for 10 successive days (once a day). The number with time of survived animals after administration and the average body weights on Days 0, 5, and 10 were determined. The results are shown in Table 11.

TABLE 11

Toxicity intraperitoneal repeated istration into mouse

| Administrered Substance | Dosage (mg/kg body weight/day x 10 days) | Number of Survived Animals | | | | | | | Fatality Rate (%) | Rate Body Weight (g) | | |
|---|---|---|---|---|---|---|---|---|---|---|---|---|
| | | Day 0 | 4 | 5 | 6 | 7 | 8 | 10 | | Day 0 | 5 | 10 |
| 0406TP-1 | 10 | 10 | 10 | 10 | 10 | 10 | 10 | 10 | 0 | 21.4 | 23.6 | 25.4 |
| | 5 | 10 | 10 | 10 | 10 | 10 | 10 | 10 | 0 | 21.8 | 23.7 | 25.5 |
| | 1 | 10 | 10 | 10 | 10 | 10 | 10 | 10 | 0 | 22.0 | 23.1 | 25.0 |
| adriamycin | 10 | 10 | 10 | 9 | 8 | 3 | 0 | 0 | 100 | 21.8 | 17.7 | — |
| | 5 | 10 | 10 | 9 | 9 | 8 | 3 | 3 | 70 | 21.6 | 21.0 | 15.8 |
| | 1 | 10 | 10 | 10 | 10 | 10 | 10 | 10 | 0 | 21.9 | 23.5 | 24.5 |
| control | — | 10 | 10 | 10 | 10 | 10 | 10 | 10 | 0 | 21.6 | 23.9 | 25.7 |

As is evident from the above results, some animals in the group given adriamycin died and their growth was inferior to the control, whereas the group given compound 0406TP-1 survived and showed a normal increase in body weight. From this result too, the low toxicity and safety of compound 0406TP-1 were suggested.

EXAMPLE 5

Production of Drip 60 mg of compound 0406TP-1 was dissolved in 60 ml of 5% D-glucose solution and this solution was combined with 440 ml of 5% D-glucose solution to give drip.

EXAMPLE 6

Production of Tablets 50 g of 0406TP-1 (1), 90 g of lactose (2), 29 g of corn starch (3), and 1 g of magnesium stearate (4) were used as starting materials to produce tablets in the following manner.

(1), (2) and 17 g of (3) were mixed and granulated together with a paste prepared from 7 g of (3). 5 g of (3), and (4), were added to the resulting granules and mixed well, and this mixture was compressed by a compression tabletting machine to produce 1000 tablets each containing 50 mg 0406TP-1 as the active ingredient.

EFFECT OF THE INVENTION

The present invention is to provide compound 0406TP-1. The present compound is a novel compound and has excellent physiological activity and can be utilized in various pharmaceutical preparations such as antitumor agent, immunosuppressive agent etc.

What is claimed is:

1. Compound 0406TP-1 represented by the formula (I):

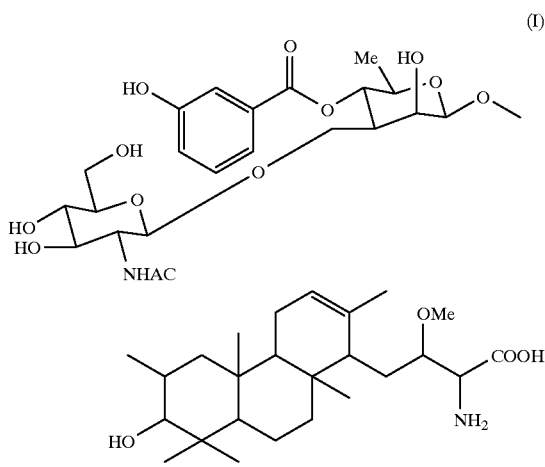

(I)

wherein Ac represents an acetyl group and Me represents a methyl group, or a pharmaceutically acceptable salt thereof.

2. An immunosupressive agent composition comprising compound 0406TP-1 as described in claim 1 or a pharmaceutically acceptable salt thereof, as the effective ingredient, and a pharmaceutically acceptable carrier or excipient.

3. An antitumor agent composition comprising compound 0406TP-1 as described in claim 1 or a pharmaceutically acceptable salt thereof, as the effective ingredient, and a pharmaceutically acceptable carrier or excipient.

4. A process for producing compound 0406TP-1 as described in claim 1 or a salt thereof, which comprises culturing *Nocardia brasiliensis* capable of producing the compound 0406TP-1 and recovering said compound from the culture.

5. The process according to claim 4, wherein said *Nocardia brasiliensis* is *Nocardia brasiliensis* IFM 0406, FERM BP-5498.

* * * * *